United States Patent
Ross, Sr.

(10) Patent No.: US 8,039,023 B1
(45) Date of Patent: Oct. 18, 2011

(54) COMPOSITION FOR RELIEF OF MENSTRUAL CRAMPS AND MUSCLE CRAMPS

(76) Inventor: Robert Gaylon Ross, Sr., Spicewood, TX (US)

( * ) Notice: Subject to any disclaimer, the term of this patent is extended or adjusted under 35 U.S.C. 154(b) by 372 days.

(21) Appl. No.: 12/420,661

(22) Filed: Apr. 8, 2009

(51) Int. Cl.
 *A61K 9/28* (2006.01)
(52) U.S. Cl. ........ 424/678; 424/449; 424/660; 424/474; 426/74
(58) Field of Classification Search ................ 424/449, 424/660, 474, 678; 426/74
See application file for complete search history.

(56) References Cited

OTHER PUBLICATIONS

Eichner, Int. J. Sports Medl 19 Suppl. 2LS150-3, Jun. 1998; Abstract.*
To-o, et al., Biosci. Biotechnol. Biochem. 67 (8), 1713-1718, 2003; p. 1713 and 1717.*
Tsugawa, et al., J. Bone Miner. Metab. 17:30-36, 1999; pp. 30 and 34.*
Turnberg, Gut, 12 811-818, 1971 pp. 811 and 816.*

* cited by examiner

*Primary Examiner* — Jean Witz
*Assistant Examiner* — Anna Falkowitz
(74) *Attorney, Agent, or Firm* — Mark W Handley

(57) ABSTRACT

A composition is disclosed which provides relief from menstrual cramps and muscle cramps within three to seven minutes after ingestion. The composition is preferably a mixture in the form of an aqueous solution with components mixed within approximately fifty percent of the following amounts: 60 mg/liter of calcium gluconate, 75 mg/liter of potassium bicarbonate, 90 mg/liter of L glutamine, 5 mg/liter of calcium chloride, 150 mg/liter of potassium chloride; 60 mg/liter of calcium ascorbate; 100 mg/liter of magnesium glycinate, and 15 mg/liter of potassium citrate. The liquid solution is taken by a human in a dosage of one to four ounces, depending upon the body weight of the person, whether the person is experiencing menstrual cramps or muscle cramps, and the area affected when the person is seeking relief from muscle cramps.

10 Claims, No Drawings

COMPOSITION FOR RELIEF OF MENSTRUAL CRAMPS AND MUSCLE CRAMPS

TECHNICAL FIELD OF THE INVENTION

The present invention relates in general to compositions for relief of discomfort, and in particular to a composition for relieving menstrual cramps and muscle cramps.

BACKGROUND OF THE INVENTION

Prior art compositions have been provided for relieving pain symptoms in humans and animals, such as for relieving menstrual cramps and muscle cramps. The prior art compositions have been administered in solid form, such as tablets and capsules, and in liquid solutions for treating pain symptoms, such as menstrual cramps and muscle cramps. These compositions include various brands of aspirin, acetaminophen and ibuprofen, which typically provide relief in the form of reduced discomfort from pain and muscle cramping symptoms after twenty to forty minutes after ingestion. A faster acting composition for directly alleviating discomfort from menstrual cramps and muscle cramps is desirable.

SUMMARY OF THE INVENTION

A composition is disclosed which provides relief from menstrual cramps and muscle cramps within three to seven minutes after ingestion. The composition is preferably a mixture in a liquid, aqueous solution which includes the following components: 60 mg/liter of calcium gluconate, 75 mg/liter of potassium bicarbonate, 90 mg/liter of L glutamine, 5 mg/liter of calcium chloride, 150 mg/liter of potassium chloride; 60 mg/liter of calcium ascorbate; 100 mg/liter of magnesium glycinate, and 15 mg/liter of potassium citrate. These amounts may be varied by approximately fifty percent above and below the listed values. The liquid solution is taken by a human in a dosage of one to four ounces, depending upon the body weight of the person, whether the person is experiencing menstrual cramps or muscle cramps, and the area affected when the person is seeking relief from muscle cramps.

DETAILED DESCRIPTION OF THE INVENTION

A composition for relief of muscle cramps is provided by combining selected components in a mixture. Preferably, the selected components of the mixture are provided in a solution with one liter distilled water as the solvent, according to the proportions set forth in Table A.

TABLE A

| Component | Amount |
| --- | --- |
| calcium gluconate | 60 mg/liter |
| potassium bicarbonate | 75 mg/liter |
| L-glutamine | 90 mg/liter |
| calcium chloride | 5 mg/liter |
| potassium chloride | 150 mg/liter |
| calcium ascorbate | 60 mg/liter |
| magnesium glycinate | 100 mg/liter |
| potassium citrate | 15 mg/liter |

A person experiencing menstrual cramps or muscle cramps will ingest preferably one to four fluid ounces of the composition in a liquid solution with water, depending upon the weight of the person and the type of muscle cramping being experienced.

The amount of each of the selected components may be varied by approximately fifty percent, with the composition maintaining effectiveness for relieving menstrual cramps and muscle cramps. Table B sets forth ranges of amounts for the selected components, based on fifty percent of the amounts listed in Table A.

TABLE B

| Component | Amount |
| --- | --- |
| calcium gluconate | (30-90) mg/liter |
| potassium bicarbonate | (37-113) mg/liter |
| L-glutamine | (45-135) mg/liter |
| calcium chloride | (3-8) mg/liter |
| potassium chloride | (75-225) mg/liter |
| calcium ascorbate | (30-90) mg/liter |
| magnesium glycinate | (50-150) mg/liter |
| potassium citrate | (7-23) mg/liter |

The components are preferably provided in commercially available food grade form, preferably in substantially pure form. Common forms of the components of the composition or solution are available from vendors listed in Table C:

TABLE C

| Component | Vendor | Vendor Part Number |
| --- | --- | --- |
| calcium gluconate | Purac America, Inc. | GLUCONAL CA |
| potassium bicarbonate | Science Lab.com | SLP1444 |
| L-glutamine | Science Lab.com | SLG1462 |
| calcium chloride | Cargill Incorporated | Calcium Chloride |
| potassium chloride | Science Lab.com | SLP3334 |
| calcium ascorbate, 20% Ca | Science Lab.com | SCL5143 |
| magnesium glycinate | Purac America, Inc. | GLUCONAL MG-P |
| potassium citrate | J M Loveridge PLC | RM209 |

The composition may be provided in powdered, capsule or tablet form. Preferably, the composition is provided as aqueous based, ionic solution. Such a solution provides for quick absorption when ingested so that relief from menstrual cramps and muscle cramps may be quickly experienced. In some embodiments, the composition may be provided as a vitamin fortified solution. The composition of the present invention preferably provides calcium, potassium, L-glutamine and magnesium in an ionic solution, with distilled water as the solvent, and the solution being substantially neutral, that is, having a PH close to 7.0. Preferred components of the composition are a mixture of the following components in the following amounts when the component listed in Table A are mixed as set forth in Table A in one liter of water: calcium 20 mg, potassium 114 mg., magnesium 14 mg, and L-glutamine 90 mg, which are substantially neutral when dissolved in solution. Preferably, these amounts of calcium 20 mg, potassium 114 mg, magnesium 14 mg, and L-glutamine 90 mg are within fifty percent, plus or minus, of the forging amounts. Relative proportions of such preferred components may be mixed in tabular form, or as a capsule, preferably in a dosage unit equal to the above-listed amounts divided by approximately 33.8 fluid ounces per liter, and a single dose being provided by one to four of such dosage units. Preferably, the dosage unit is mixed in one fluid ounce or water, or in the alternative, ingested with water.

Calcium gluconate, calcium chloride and calcium ascorbate provide ionic calcium. Chronic calcium deficiencies have been associated with some forms of menstrual and pre-menstrual symptoms. Calcium deficiencies may also result from high protein or phosphate levels, such occur with kidney disease, poor diet, hormonal diseases, hormonal imbalances, nutritional imbalances (such as a high Mg/Ca ratio, and low pantothenic acid), celiac disease or other intestinal conditions which interfere with calcium absorption. Prescribed medications may also promote calcium deficiencies, as well as random self-supplementation of the wrong vitamins and minerals. Calcium is a mineral which plays a role in the development and integrity of bones and teeth, heart rhythm, blood clotting, nerve and muscle function, blood pressure, kidney function, and cholesterol levels.

Potassium bicarbonate, potassium chloride and potassium citrate provide ionic potassium. Potassium bicarbonate is an electrolyte which provides potassium for increased potassium blood levels. Potassium chloride is also an electrolyte replenisher. Potassium citrate is a mineral supplement for preventing or treat low amounts of potassium in the blood. A normal level of potassium in the blood is important for cell, nerve, heart, muscles, and kidney function.

L-glutamine provides glycogen for storing in the body. Prolonged exercise is known to lower glycogen levels in the body, and taking L-glutamine before or after workouts helps the body store more glycogen, which provides the energy reserve in the liver and muscle that fuels exercise. L-glutamine also prevents muscle soreness and increases the rate of muscle recovery after exercise.

Magnesium glycinate provides a source for replenishing magnesium. Magnesium is lost during exercise, and loss of magnesium which may be accelerated during endurance exercise.

Tests of a composition made according to the present invention have shown complete relief from menstrual cramps and muscle cramps within three to seven minutes after ingestion of the composition. A test subject will first experience a warming or heating sensation in the area of pain from muscle cramping, and then shortly thereafter, will experience relief from the muscle cramps. Relief from cramping typically last for several hours, and then the composition may be administered again. In some cases, relief from menstrual cramps and muscle cramps may last for several days without further ingestion of the composition made according to the present invention.

In one test, a subject who works as a waitress was experiencing lower back pain and foot pain from muscle cramps as a result of extended hours on her feet. Within two minutes of ingesting the composition, her lower back pain from cramping was no longer felt. After five minutes she no longer experienced foot pain from cramping. Previously administered medications had been ineffective in reducing pain in the subject. The test subject experienced complete and total relief from the discomfort of cramps within five minutes of ingesting the composition made according to the present invention.

In a second test, a subject who has undergone more than one back surgery would have cramps in his lower back, thighs and calves. Cramping in his tail bone would often present severe pain which was only relieved by massage and brisk walking, once he could again walk after experiencing the onset of pain. Mediation failed to provide relief. The subject would often experience such pain that he could only lay in a fetal position, and could not walk until after initial massaging relieved the pain. In such as session, the subject was pain free and able to walk within three to seven minutes after ingesting the composition, and without massaging the affected area. That is, the test subject experienced complete and total relief from the discomfort of cramps within seven minutes of ingesting the composition made according to the present invention, when conventional medication had been ineffective.

Another test was performed with a post-menopausal test subject who has experienced headaches due to muscle tension, presumed to be caused by hormonal imbalances. Ingesting the composition made according to the present invention has been found to relieve the pain from the headaches, providing relief which had not been effected by prescribed medications.

Yet another test performed with a female test subject who experiences headaches attributed to hormones, and for whom migraine pain medication had previously been prescribed. She has found that the migraine pain medication usually takes approximately twenty minutes or longer after ingestion to become effective, and that symptoms persisted after the migraine pain medication became effective. The test subject has found that the composition made according the to the present invention is effective to stop the pain in a little more than six minutes, and provided more effective relief than the prescribed medication. The test subject experienced complete and total relief from the discomfort of the headaches after ingesting the composition.

In still another test performed on a female subject who experienced severe menstrual discomfort, complete relief was experienced within three minutes. The subject previously often could not eat, experienced constant headaches and would frequently throw up after eating for a period of five days during her menstrual cycle. The composition according to the present invention provided complete and total relief from such symptoms where medication was ineffective.

For several other test subject, pain from menstrual, leg and neck cramps which previously had not responded to pain medication were quickly relieved. In most circumstances, complete and total relief was experienced in three to seven minutes, even for those subject for whom conventional pain medication had been ineffective.

The results of the above-noted field trials with human subjects determined that ingesting one to four ounces of the composition resulted in relieving most muscle cramps; about 70-80% of painful menstrual cramps; some migraine headaches; some lower back pains; and some cases of numb or tingling feet in the test subjects. Complete and total relief was experienced within three to seven minutes after consuming the composition. Typically, relief is felt as a warming sensation and then total relief from the sensation of muscle cramps.

The present invention provides advantages of fast acting relief from discomfort caused by menstrual cramps and muscle cramps. Persons ingesting the composition provided by the mixture of the present invention experience complete and total relief from menstrual cramps and muscle cramps within three to seven minutes after ingestion of one to four ounces of the mixture, according to body weight and the type of cramping experienced. The composition is made by mixing food grade products providing the components according to the amounts noted above.

Although the preferred embodiment has been described in detail, it should be understood that various changes, substitutions and alterations can be made therein without departing from the spirit and scope of the invention as defined by the appended claims.

What is claimed is:

1. A composition for relief of cramps, comprising:

| Component | Amount |
| --- | --- |
| calcium gluconate | (30-90) mg/liter |
| potassium bicarbonate | (37-113) mg/liter |

-continued

| Component | Amount |
|---|---|
| L-glutamine | (45-135) mg/liter |
| calcium chloride | (3-8) mg/liter |
| potassium chloride | (75-225) mg/liter |
| calcium ascorbate | (30-90) mg/liter |
| magnesium glycinate | (50-150) mg/liter |
| potassium citrate | (7-23) mg/liter | wherein said components are configured for administering for the subject experiencing the cramps.

2. The composition according to claim 1, wherein said components are suspended in a solution.

3. The composition according to claim 2, wherein water provides a solvent for said solution.

4. The composition according to claim 3, wherein said solution is in liquid form at room temperatures.

5. The composition according to claim 1, wherein the said components are suspended in a solution and said solution is in liquid form at room temperatures.

6. A composition for relief of cramps, in which a mixture is formed comprising the following:

| Component | Amount |
|---|---|
| calcium gluconate | 60 mg/liter |
| potassium bicarbonate | 75 mg/liter |
| L-glutamine | 90 mg/liter |
| calcium chloride | 5 mg/liter |
| potassium chloride | 150 mg/liter |
| calcium ascorbate | 60 mg/liter |
| magnesium glycinate | 100 mg/liter |
| potassium citrate | 15 mg/liter | wherein said mixture is configured for administering to a subject experiencing the cramps.

7. The composition according to claim 6, wherein said mixture is suspended in a solution.

8. The composition according to claim 7, wherein water provides a solvent for said solution.

9. The composition according to claim 8, wherein said solution is in liquid form at room temperatures.

10. The composition according to claim 6, wherein the said mixture is suspended in a solution and said solution is in liquid form at room temperatures.

* * * * *